(12) United States Patent
Keener et al.

(10) Patent No.: US 10,729,798 B2
(45) Date of Patent: Aug. 4, 2020

(54) INACTIVATING PATHOGENIC MICROORGANISMS USING COLD PLASMA

(71) Applicant: Purdue Research Foundation, West Lafayette, IN (US)

(72) Inventors: Kevin Michael Keener, Ames, IA (US); Nikhil K Mahnot, Assam (IN)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/302,436

(22) PCT Filed: May 15, 2017

(86) PCT No.: PCT/US2017/032691
§ 371 (c)(1),
(2) Date: Nov. 16, 2018

(87) PCT Pub. No.: WO2017/200930
PCT Pub. Date: Nov. 23, 2017

(65) Prior Publication Data
US 2019/0290792 A1     Sep. 26, 2019

Related U.S. Application Data

(60) Provisional application No. 62/338,680, filed on May 19, 2016.

(51) Int. Cl.
*A61L 2/14* (2006.01)
*A23L 2/02* (2006.01)
(Continued)

(52) U.S. Cl.
CPC .................. *A61L 2/14* (2013.01); *A23L 2/02* (2013.01); *A23L 2/50* (2013.01); *A23L 3/26* (2013.01); *A61L 2/0011* (2013.01); *C02F 1/4608* (2013.01); *H05H 1/00* (2013.01); *H05H 1/2406* (2013.01); *A23V 2002/00* (2013.01); *A61L 2202/11* (2013.01); *A61L 2202/21* (2013.01);
(Continued)

(58) Field of Classification Search
CPC . A61L 2/24; A61L 2/14; A61L 2/0011; A23L 2/02; A23L 2/50; A23L 3/26
See application file for complete search history.

(56) References Cited

U.S. PATENT DOCUMENTS 5,876,663 A * 3/1999 Laroussi ............... A23L 3/005
                                                           204/164
8,961,894 B2 * 2/2015 Keener .................. A61L 2/14
                                                           422/305

OTHER PUBLICATIONS

Yamazaki et al., "Microbicidal activites of low frequency atmospheric pressure plasma jets on oral pathogens", Dental Materials Journal, vol. 30(3), published 2011, pp. 384-391.*

(Continued)

*Primary Examiner* — Sean E Conley
(74) *Attorney, Agent, or Firm* — Purdue Research Foundation; Liang Zeng Yan (57) ABSTRACT

This present invention generally relates to a process for manipulating the chemistry of a product using high voltage atmospheric cold plasma (HVACP) in the presence of a working gas, and in particular to a process for inactivating pathogenic microorganisms in a liquid product by adding an acidic component to or adjusting an acidic component of a product in combination with HVACP treatment. A product of this process is also in the scope of this disclosure.

21 Claims, 4 Drawing Sheets

(51) Int. Cl.
- A23L 2/50 (2006.01)
- A23L 3/26 (2006.01)
- A61L 2/00 (2006.01)
- C02F 1/46 (2006.01)
- H05H 1/24 (2006.01)
- H05H 1/00 (2006.01)

(52) U.S. Cl.
CPC .. C02F 2303/04 (2013.01); H05H 2001/2412 (2013.01)

(56) References Cited

OTHER PUBLICATIONS

Yamazaki, et al., "Microbicidal activities of low frequency atmospheric pressure plasma jets on oral pathogens". Dental Materials Journal 2011, 303(3): 384-391.

Ikawa, et al., "Effects of pH on Bacterial Inactivation in Aqueous Solutions." Plasma Processes and Polymers, 2010, 7, 33-42.

Kogelschatz, U. "Dielectric-barrier Discharges", Plasma Chemistry and Plasma Processing, 2003, 23(1), 1-46.

Oehmigen, et al., "The Role of Acidification for Antimicrobial Activity of Atmospheric Pressure Plasma in Liquids". Plasma Processes and Polymers, 2010, 7, 250-257.

Kim, et al., "Microbial safety and quality attributes of milk following treatment with atmospheric pressure encapsulated diaelectric barrier discharge plasma." Food Control, 2015, 47, 451-456.

Young, et al., "The Chemical Coposition and Biological Properties of Coconut water". Molecules 2009, 14, 5144-5164.

Surowsky, et al., "Impact of cold plasma on Citrobacter freundii in apple juice" Int'l J. Food Microbial. 2014, 174, 63-71.

Mahnot, et al., "Effect of additives on the quality of tender coconut water processed by nonthermal two stage microfiltration technique." LWT—Food Science and Technology, 2014, 59, 1191-1195.

Purkayastha, et al., "Effect of L-ascorbic acid addition on the quality attributes of micro-filtered coconut water stored at 4 degree." Innovative Food Science and Emerging Technologies 2012, 16,69-79.

Almeida, et al., "Effects of atmospheric cold plasma and ozone on prebiotic orange jusice." Innovative Food Science and Emerging Technologies 2015, 32, 127-135.

67394-02 _ISR_and_Written_opinion.

* cited by examiner

INACTIVATING PATHOGENIC MICROORGANISMS USING COLD PLASMA

CROSS-REFERENCE TO RELATED APPLICATIONS

The present U.S. patent application is a national stage entry under 35 U.S.C. § 371(b) of International Application No. PCT/US17/32691, filed on May 15, 2017, which claims priority under 35 U.S.C. § 119(e) to the U.S. Provisional Application No. 62/338,680, filed on May 19, 2016, the contents of which are hereby incorporated by reference in their entirety into the present disclosure.

TECHNICAL FIELD

The present disclosure generally relates to a process for manipulating the chemistry of a product using high voltage atmospheric cold plasma (HVACP) in the presence of a working gas, and in particular to a process for inactivating pathogenic microorganisms in a liquid product by adding an acidic component to or adjusting an acidic component of a product in combination with HVACP treatment.

BACKGROUND

This section introduces aspects that may help facilitate a better understanding of the disclosure. Accordingly, these statements are to be read in this light and are not to be understood as admissions about what is or is not prior art.

Atmospheric cold plasma (ACP) technology has been getting more importance as a non-thermal processing technique to inactivate pathogenic microbes in food products (Surowsky, et al., *Int'l J. Food Microbiol.* 174 (2014) 63-71). The technique utilizes an electrical discharge between two electrodes which lead to generation of cold plasma, a source of electrons, ions, UV light, and reactive gas species, which assist inactivating pathogenic microbes and therefore offer a useful sterilization process. Atmospheric cold plasma has been applied to a wide range of food products, including cheese, lettuce, egg shells, blue berries, strawberries, ham, pork loins, and bacon (ibid.), and liquid products, such as milk, juices (Almeida, et al., *Innovative Food Science and Emerging Technologies*, 32 (2015), 127-135; Kim, et al., *Food Control* 47(2015) 451-456).

However, recent studies have suggested that practical uses of ACP in liquid foods sterilization is still a challenge. Work conducted on liquid foods like milk, apple juice and orange juice has shown some positive results in killing microbes. Currently there are no reports on processing tender coconut water using high voltage atmospheric cold plasma, even though other techniques like thermal and non-thermal technologies has been reported in literature (N. K. Mahnot et al., *LWT-Food Science and Technology*, 59(2), 1191-1195 (2014)).

The coconut is an important fruit tree in the tropical regions. The edible parts of the coconut fruit, including coconut meat and coconut water, is the endosperm tissue (Yong, et al., *Molecules* 2009, 14, 5144-5164). Coconut water is of cytoplasmic origin, which should not be confused with coconut milk obtained from grating the solid endosperm (meat). Even though coconut water is mainly water (ca. 94%), it contains significant and most useful components, such as phytohormones, micronutrients (including inorganic ions and vitamins), sugars, sugar alcohols, lipids, amino acids, organic acids and enzymes (ibid.). Therefore coconut water is widely consumed due to its beneficial properties to health. It is also believe that coconut water could be used as an important alternative for oral rehydration and may offer protection against myocardial infarction. In addition, coconut water is widely used in the plant tissue culture industry (ibid.).

In order to take advantage of the benefits of coconut water, a sterilized, pathogen-free product is most desirable for human and animal consumption. There are still unmet needs on further improvement of the current process to prepare safe liquid food products for human and animal that meet the requirements of the Food and Drug Administration (FDA) achieving a 5-log bacterial reduction (www.fda.gov/Food/GuidanceRegulation/).

BRIEF SUMMARY OF INVENTION

In some embodiments, this invention relates to a process for manipulating a product using high voltage atmospheric cold plasma (HVACP), comprising the steps of:
 a. Adding or adjusting an acidic component in said product to a final concentration from about 10 ppm to about 50,000 ppm;
 b. Setting up a defined compartment filled with a working gas;
 c. Generating atmospheric cold plasma (ACP) by applying a high electric voltage through a controller; and
 d. Exposing said product to ACP in said defined compartment.

In some embodiments, this invention relates to a process for manipulating a product using high voltage atmospheric cold plasma (HVACP) disclosed herein, wherein said atmospheric cold plasma (ACP) is generated by applying an electric voltage from about 5,000 volts to about 200,000 volts between two dielectric barriers for a period of time.

In some preferred embodiments, this invention relates to a process for manipulating a product using high voltage atmospheric cold plasma (HVACP) disclosed herein, wherein said ACP is generated by applying an electric voltage from about 30,000 volts to about 120,000 volts between two dielectric barriers for a period of time.

In some preferred embodiments, this invention relates to a process for manipulating a product using high voltage atmospheric cold plasma (HVACP) disclosed herein, wherein said manipulating is to inactivate or kill pathogenic and non-pathogenic microorganisms in said product for consumption by human or animal.

In some embodiments, this invention relates to a process for manipulating a product using high voltage atmospheric cold plasma (HVACP) disclosed herein, wherein said working gas is a single or a mixture of combined gases including, but not limited to, air, hydrogen, nitrogen, oxygen, carbon dioxide, noble gases, or a combination thereof.

In some preferred embodiments, this invention relates to a process for manipulating a product using high voltage atmospheric cold plasma (HVACP) disclosed herein, wherein said working gas is air.

In some preferred embodiments, this invention relates to a process for manipulating a product using high voltage atmospheric cold plasma (HVACP) disclosed herein, wherein said working gas is a modified air comprising about 65% oxygen, about 30% carbon dioxide, and about 5% nitrogen.

In some preferred embodiments, this invention relates to a process for manipulating a product using high voltage atmospheric cold plasma (HVACP) disclosed herein, wherein said acid component is selected from the group consisting of acetic acid, ascorbic acid, benzoic acid, carbonic acid, citric acid, glutamic acid, glycolic acid, hydrochloric acid, lactic acid, malic acid, oxalic acid, propionic acid, tartaric acid, natural amino acids, or a combination of two or more of said acids.

In some preferred embodiments, this invention relates to a process for manipulating a product using high voltage atmospheric cold plasma (HVACP) disclosed herein, wherein said acid component is citric acid.

In some preferred embodiments, this invention relates to a process for manipulating a product using high voltage atmospheric cold plasma (HVACP) disclosed herein, wherein said product is a food or drink product for consumption by human or animal.

In some preferred embodiments, this invention relates to a process for manipulating a product using high voltage atmospheric cold plasma (HVACP) disclosed herein, wherein said product is a liquid product.

In some embodiments, this invention relates to a process for manipulating a product using high voltage atmospheric cold plasma (HVACP) disclosed herein, wherein said product is a liquid product for cleaning, washing, or dressing solution for food, feed, medical, pharmaceutical industries, or household uses.

In some preferred embodiments, this invention relates to a process for manipulating a product using high voltage atmospheric cold plasma (HVACP) disclosed herein, wherein said product is a liquid product selected from the group of water, carbonated water, coconut water, tender coconut water, fruit juices, vegetable juices, mixed fruit juices, mixed vegetable juices, mixed fruit and vegetable juices, sports drinks, saline water, rehydration liquid formulations, milk, liquid milk products, alcoholic beverages, and fermented beverages.

In some preferred embodiments, this invention relates to a process for manipulating a product using high voltage atmospheric cold plasma (HVACP) disclosed herein, wherein said liquid product is water or coconut water.

In some other embodiments, this invention relates to a product prepared according to the process disclosed herein, using high voltage atmospheric cold plasma (HVACP), promising the steps of:
  a. adding an acidic component to or adjusting an acidic component of a product to a final concentration from about 10 ppm to about 50,000 ppm;
  b. setting up a defined compartment filled with a working gas and an electric system for generating atmospheric cold plasma (ACP);
  c. generating ACP by applying a high electric voltage through a controller; and
  d. exposing said product to said ACP in said defined compartment.

In some embodiments, this invention relates to a product prepared according to the process disclosed herein, using high voltage atmospheric cold plasma (HVACP), wherein said product is a liquid product.

In some embodiments, this invention relates to a product prepared according to the process disclosed herein, using high voltage atmospheric cold plasma (HVACP), wherein said product is a liquid product for cleaning, washing, or dressing solution for food, feed, medical, pharmaceutical industries, or household uses.

In some embodiments, this invention relates to a product prepared according to the process disclosed herein, using high voltage atmospheric cold plasma (HVACP), wherein said liquid product is a liquid food product comprising water, carbonated water, coconut water, tender coconut water, fruit juices, vegetable juices, mixed fruit juices, mixed vegetable juices, mixed fruit and vegetable juices, sports drinks, saline water, rehydration liquid formulations, milk, liquid milk products, alcoholic beverages, including beer, wines, ciders, or the like.

In some embodiments, this invention relates to a product prepared according to the process disclosed herein, using high voltage atmospheric cold plasma (HVACP), wherein said product is water or coconut water.

In some embodiments, this invention relates to a product prepared according to the process disclosed herein, using high voltage atmospheric cold plasma (HVACP), wherein said acidic component comprises acetic acid, ascorbic acid, benzoic acid, carbonic acid, citric acid, glutamic acid, glycolic acid, hydrochloric acid, lactic acid, malic acid, oxalic acid, propionic acid, tartaric acid, natural amino acids, or a combination of two or more of said acids.

In some embodiments, this invention relates to a product prepared according to the process disclosed herein, using high voltage atmospheric cold plasma (HVACP), wherein said working gas is a single or combined gases including, but not limited to, air, hydrogen, nitrogen, oxygen, carbon dioxide, noble gases, or a combination thereof.

In some embodiments, this invention relates to a product prepared according to the process disclosed herein, using high voltage atmospheric cold plasma (HVACP), wherein said working gas is air.

In some embodiments, this invention relates to a product prepared according to the process disclosed herein, using high voltage atmospheric cold plasma (HVACP), wherein said working gas is a modified air comprising about 65% oxygen, about 30% carbon dioxide, and about 5% nitrogen.

In some embodiments, this invention relates to a product prepared according to the process disclosed herein, using high voltage atmospheric cold plasma (HVACP), wherein said atmospheric cold plasma (ACP) is generated by applying an electric voltage from about 5,000 volts to about 200,000 volts between two dielectric barriers for a period of time.

In some preferred embodiments, this invention relates to a product prepared according to the process disclosed herein, using high voltage atmospheric cold plasma (HVACP), wherein said atmospheric cold plasma (ACP) is generated by applying an electric voltage from about 30,000 volts to about 120,000 volts between two dielectric barriers for a period of time.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In some embodiments, this invention relates to a process for manipulating a product using high voltage atmospheric cold plasma (HVACP), comprising the steps of:
  a. Adding or adjusting an acidic component in said product to a final concentration from about 10 ppm to about 50,000 ppm;
  b. Setting up a defined compartment filled with a working gas;
  c. Generating atmospheric cold plasma (ACP) by applying a high electric voltage through a controller; and
  d. Exposing said product to ACP in said defined compartment.

In some embodiments, this invention relates to a process for manipulating a product using high voltage atmospheric cold plasma (HVACP) disclosed herein, wherein said atmospheric cold plasma (ACP) is generated by applying an electric voltage from about 5,000 volts to about 200,000 volts between two dielectric barriers for a period of time.

In some preferred embodiments, this invention relates to a process for manipulating a product using high voltage atmospheric cold plasma (HVACP) disclosed herein, wherein said ACP is generated by applying an electric voltage from about 30,000 volts to about 120,000 volts between two dielectric barriers for a period of time.

In some preferred embodiments, this invention relates to a process for manipulating a product using high voltage atmospheric cold plasma (HVACP) disclosed herein, wherein said manipulating is to inactivate or kill pathogenic and non-pathogenic microorganisms in said product for consumption by human or animal.

In some embodiments, this invention relates to a process for manipulating a product using high voltage atmospheric cold plasma (HVACP) disclosed herein, wherein said working gas is a single or a mixture of combined gases including, but not limited to, air, hydrogen, nitrogen, oxygen, carbon dioxide, noble gases, or a combination thereof.

In some preferred embodiments, this invention relates to a process for manipulating a product using high voltage atmospheric cold plasma (HVACP) disclosed herein, wherein said working gas is air.

In some preferred embodiments, this invention relates to a process for manipulating a product using high voltage atmospheric cold plasma (HVACP) disclosed herein, wherein said working gas is a modified air comprising about 65% oxygen, about 30% carbon dioxide, and about 5% nitrogen.

In some preferred embodiments, this invention relates to a process for manipulating a product using high voltage atmospheric cold plasma (HVACP) disclosed herein, wherein said acid component is selected from the group consisting of acetic acid, ascorbic acid, benzoic acid, carbonic acid, citric acid, glutamic acid, glycolic acid, hydrochloric acid, lactic acid, malic acid, oxalic acid, propionic acid, tartaric acid, natural amino acids, or a combination of two or more of said acids.

In some preferred embodiments, this invention relates to a process for manipulating a product using high voltage atmospheric cold plasma (HVACP) disclosed herein, wherein said acid component is citric acid.

In some preferred embodiments, this invention relates to a process for manipulating a product using high voltage atmospheric cold plasma (HVACP) disclosed herein, wherein said product is a food or drink product for consumption by human or animal.

In some preferred embodiments, this invention relates to a process for manipulating a product using high voltage atmospheric cold plasma (HVACP) disclosed herein, wherein said product is a liquid product.

In some embodiments, this invention relates to a process for manipulating a product using high voltage atmospheric cold plasma (HVACP) disclosed herein, wherein said product is a liquid product for cleaning, washing, or dressing solution for food, feed, medical, pharmaceutical industries, or household uses.

In some preferred embodiments, this invention relates to a process for manipulating a product using high voltage atmospheric cold plasma (HVACP) disclosed herein, wherein said product is a liquid product selected from the group of water, carbonated water, coconut water, tender coconut water, fruit juices, vegetable juices, mixed fruit juices, mixed vegetable juices, mixed fruit and vegetable juices, sports drinks, saline water, rehydration liquid formulations, milk, liquid milk products, alcoholic beverages, and fermented beverages.

In some preferred embodiments, this invention relates to a process for manipulating a product using high voltage atmospheric cold plasma (HVACP) disclosed herein, wherein said liquid product is water or coconut water.

In some other embodiments, this invention relates to a product prepared according to the process disclosed herein, using high voltage atmospheric cold plasma (HVACP), promising the steps of:
  a. adding an acidic component to or adjusting an acidic component of a product to a final concentration from about 10 ppm to about 50,000 ppm;
  b. setting up a defined compartment filled with a working gas and an electric system for generating atmospheric cold plasma (ACP);
  c. generating ACP by applying a high electric voltage through a controller; and
  d. exposing said product to said ACP in said defined compartment.

In some embodiments, this invention relates to a product prepared according to the process disclosed herein, using high voltage atmospheric cold plasma (HVACP), wherein said product is a liquid product.

In some embodiments, this invention relates to a product prepared according to the process disclosed herein, using high voltage atmospheric cold plasma (HVACP), wherein said product is a liquid product for cleaning, washing, or dressing solution for food, feed, medical, pharmaceutical industries, or household uses.

In some embodiments, this invention relates to a product prepared according to the process disclosed herein, using high voltage atmospheric cold plasma (HVACP), wherein said liquid product is a liquid food product comprising water, carbonated water, coconut water, tender coconut water, fruit juices, vegetable juices, mixed fruit juices, mixed vegetable juices, mixed fruit and vegetable juices, sports drinks, saline water, rehydration liquid formulations, milk, liquid milk products, alcoholic beverages, including beer, wines, ciders, or the like.

In some embodiments, this invention relates to a product prepared according to the process disclosed herein, using high voltage atmospheric cold plasma (HVACP), wherein said product is water or coconut water.

In some embodiments, this invention relates to a product prepared according to the process disclosed herein, using high voltage atmospheric cold plasma (HVACP), wherein said acidic component comprises acetic acid, ascorbic acid, benzoic acid, carbonic acid, citric acid, glutamic acid, glycolic acid, hydrochloric acid, lactic acid, malic acid, oxalic acid, propionic acid, tartaric acid, natural amino acids, or a combination of two or more of said acids.

In some embodiments, this invention relates to a product prepared according to the process disclosed herein, using high voltage atmospheric cold plasma (HVACP), wherein said working gas is a single or combined gases including, but not limited to, air, hydrogen, nitrogen, oxygen, carbon dioxide, noble gases, or a combination thereof.

In some embodiments, this invention relates to a product prepared according to the process disclosed herein, using high voltage atmospheric cold plasma (HVACP), wherein said working gas is air.

In some embodiments, this invention relates to a product prepared according to the process disclosed herein, using high voltage atmospheric cold plasma (HVACP), wherein said working gas is a modified air comprising about 65% oxygen, about 30% carbon dioxide, and about 5% nitrogen.

In some embodiments, this invention relates to a product prepared according to the process disclosed herein, using high voltage atmospheric cold plasma (HVACP), wherein said atmospheric cold plasma (ACP) is generated by applying an electric voltage from about 5,000 volts to about 200,000 volts between two dielectric barriers for a period of time.

In some preferred embodiments, this invention relates to a product prepared according to the process disclosed herein, using high voltage atmospheric cold plasma (HVACP), wherein said atmospheric cold plasma (ACP) is generated by applying an electric voltage from about 30,000 volts to about 120,000 volts between two dielectric barriers for a period of time.

In some other embodiments, this invention relates to a method for inactivating a pathogenic and non-pathogenic microorganism in a product, the method comprises the steps of:
  a. adding an acidic component to or adjusting an acidic component of a product to a final concentration from about 10 ppm to about 50,000 ppm;
  b. setting up a defined compartment filled with a working gas and an electric system for generating atmospheric cold plasma (ACP);
  c. generating ACP by applying a high electric voltage through a controller; and
  d. Exposing said product to said ACP in said defined compartment.

In some other embodiments, this invention relates to a method for inactivating a pathogenic and non-pathogenic microorganism in a product disclosed herein, wherein said product is a liquid product.

In some embodiments, this invention relates to a method for inactivating a pathogenic and non-pathogenic microorganism disclosed herein, wherein said product is a liquid product for cleaning, washing, or dressing solution for food, feed, medical, pharmaceutical industries, or household uses.

In some other embodiments, this invention relates to a method for inactivating a pathogenic and non-pathogenic microorganism in a product disclosed herein, wherein said liquid product is a liquid product comprising water, carbonated water, coconut water, tender coconut water, fruit juices, vegetable juices, mixed fruit juices, mixed vegetable juices, mixed fruit and vegetable juices, sports drinks, saline water, rehydration liquid formulations, milk, liquid milk products, alcoholic beverages, including beer, wines, ciders, or the like.

In some embodiments, this invention relates to a method for inactivating a pathogenic and non-pathogenic microorganism in a product disclosed herein, wherein said product is water or coconut water.

In some other embodiments, this invention relates to a method for inactivating a pathogenic and non-pathogenic microorganism in a product disclosed herein, wherein said acid component is selected from the group consisting of acetic acid, ascorbic acid, benzoic acid, carbonic acid, citric acid, glutamic acid, glycolic acid, hydrochloric acid, lactic acid, malic acid, oxalic acid, propionic acid, tartaric acid, natural amino acids, or a combination of any two or more of said acids.

In some embodiments, this invention relates to a method for inactivating a pathogenic and non-pathogenic microorganism in a product disclosed herein, wherein said working gas is a single or combined gases including, but not limited to, air, hydrogen, nitrogen, oxygen, carbon dioxide, noble gases, or a combination thereof.

In some preferred embodiments, this invention relates to a method for inactivating a pathogenic and non-pathogenic microorganism in a product disclosed herein, wherein said working gas is air.

In some other embodiments, this invention relates to a method for inactivating a pathogenic and non-pathogenic microorganism in a product disclosed herein, wherein said working gas is a modified air comprising about 65% oxygen, about 30% carbon dioxide, and about 5% nitrogen.

In some other embodiments, this invention relates to a system for inactivating a pathogenic and non-pathogenic microorganism in a product disclosed herein, using high voltage atmospheric cold plasma (HVACP), the system comprises a controller, a high voltage transformer and a controller, a defined compartment for housing electrodes connected to said high voltage transformer and controller, a working gas, and said liquid product for HVACP treatment.

In some other embodiments, this invention relates to a system for inactivating a pathogenic and non-pathogenic microorganism in a product disclosed herein, using high voltage atmospheric cold plasma (HVACP), the system comprises a controller, wherein said liquid product is a product for mammal consumption containing an acidic component at a final concentration ranging from about 10 ppm to about 50,000 ppm.

In some preferred embodiments, this invention relates to a system for inactivating a pathogenic and non-pathogenic microorganism in a product disclosed herein, using high voltage atmospheric cold plasma (HVACP), wherein said product is a liquid product.

In some preferred embodiments, this invention relates to a system for inactivating a pathogenic and non-pathogenic microorganism in a product disclosed herein, using high voltage atmospheric cold plasma (HVACP), wherein said liquid product is water or coconut water.

In the interest of clarity, not all the routine features of the examples herein are described. It will of course be appreciated that in the development of any such actual implementation, numerous implementation-specific decisions must be made to achieve a developer's specific goals, such as consideration of system, regulatory, and business related constraints. These goals will vary from one implementation to another.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 80%, within 90%, within 95%, or within 99% of a stated value or of a stated limit of a range.

All current described herein is alternating current, specified as volts (V) and kilovolts (kV) root mean squared (RMS). Percent (%) gas compositions are in volume percentages.

A cold plasma refers to plasma which has a temperature of at most 40° C. above the temperature of the gas used to prepare the plasma (that is, the working gas), more preferably a temperature of at most 20° C. above the temperature of the gas used to prepare the plasma.

High-voltage cold plasma (HVCP) means a cold plasma prepared using a dielectric barrier discharge (DBD) system, using voltages of at most 500 kV, with a frequency at most to 1000 Hz, prepared from a gas having a pressure of 10 to 50000 Torr, such as 760 Torr (atmospheric pressure). HVCP is not a thermal plasma, is not a microwave plasma and is not a radio frequency (RF) plasma. HVCP plasmas are prepared under non-equilibrium breakdown conditions.

Dielectric barrier discharge (DBD), or a DBD system, means a system having at least two electrodes separated by a dielectric barrier, and may have more electrodes, where a dielectric barrier is present between each electrode, to prevent charge generated in the gas by a discharge from reaching an electrode. The shortest distance between adjacent electrodes in a DBD system is preferably at most 30 cm (or 12 inches), and preferably is at least 0.5 cm (~0.25 inches). Preferably, DBD systems are configures to operate under conditions to produce an HVCP.

High Voltage Atmospheric Cold Plasma (HVACP):

Plasma is defined as the fourth state of matter. Atmospheric cold plasma (ACP) is a natural phenomenon that has been converted into a valuable technology. The Northern Lights (aurora borealis) is a cold plasma resulting from charged particles emitted from the sun interacting with the earth's magnetic field and causing ionization.

Industrial applications of atmospheric cold plasma have been in use for over 150 years. The first atmospheric, cold plasma was invented by Werner von Siemens in 1857 (W. Siemens, Poggendorff's *Ann. Phys.* Chem. 102, 66 (1857)). This system was a dielectric barrier discharge system where air was passed between two parallel plates, with a voltage differential to generate ozone and used for water treatment (U. Kogelschatz, Plasma Chemistry and Plasma Processing, Vol. 23, No. 1, 1-46 (2003)). Plasmas can be generated in any gas environments (examples are air, $O_2$, $H_2$, $N_2$, and $CO_2$) with either direct current (DC) or alternating current (AC).

ACP has found applications for use in areas including surface cleaning, surface property alteration, air cleaning, automobile exhaust gas cleaning, UV generation, ozone production, etc. ACP capitalizes on the chemical properties of gases and the physics of electric fields. When voltage gradients of adequate strength are experienced by a gas; a few gas molecules can be stripped of a free electron (ionization). These electrons then proceed to be reactive with the bulk gas generating light, UV, and unique reactive gas species (ozone, nitric oxides, peroxides, atomic oxygen, etc.) many of which have bactericidal properties. There are many different types of ACP systems, and these are characterized by the plasma formation. Examples of ACP's would include plasma jet, microwave plasma, dielectric barrier discharge (DBD), and corona discharge.

Atmospheric pressure "cold" plasmas have been shown to be effective in reducing or eliminating surface bacterial contamination of food samples. The term "cold plasma" is meant to describe a plasma discharge, which may be atmospheric non-equilibrium plasma (ANEP), occurring at a pressure of about one-atmosphere and at near ambient temperature. This is to distinguish the ANEP plasma from a thermal plasma discharge operating at a bulk gas temperature of hundreds or thousands of degrees above the ambient temperature. In a "cold plasma" at atmospheric pressure the electrons may have a significantly higher temperature than the ion and neutral species; however, the bulk temperature of the working gas is not significantly increased with respect to the ambient temperature. In this context, the term "cold" should not be interpreted to require refrigeration or other cooling to perform the decontamination or treatment functions described herein; however, this does not exclude the treating or the subsequent storage of the treated object at an appropriate temperature, which may include refrigeration or cooling. Keeping the gas at a near ambient temperature may contribute to avoidance of heat damage to the object being treated.

One technique of creating an atmospheric non-equilibrium plasma is to apply a high voltage to the volume to be ionized, while inhibiting the transition from a glow discharge to an arc discharge by limiting the discharge current. This may be done, for example, by covering at least one of the electrodes of the apparatus with a dielectric layer; resistive layers have also been used. The discharge current is self-limited by charge build up on the dielectric surface. Typically, the excitation voltage frequency is in the kHz range, but may range from power line frequencies to microwave frequencies. The experimental data presented herein used a 60 Hz frequency due to the availability of high voltage transformers, whose output voltage could be easily be adjusted by controlling the input voltage thereof with a variable voltage transformer. The voltage for this cold plasma generation purpose normally ranges from about 5,000 volts (5 kV) to about 500 kV, preferably from about 30 kV to about 120 kV, having a frequency of at most 1000 Hz, more preferably 10 to 100 Hz, such as 50 to 60 Hz, with a DBD system.

Dielectric-barrier discharges (DBD) are a type of alternating-current high voltage gaseous discharges that may be formed in a nominally atmospheric pressure environment. The presence of a dielectric layer between the electrodes prevents the charge generated in the gas by the discharge from reaching at least one of the conducting electrode surfaces. Often the dielectric layer is applied to both of the electrodes. Within each half-cycle of the driving voltage waveform, when the voltage gradient applied across the gas exceeds that required for breakdown, the formation of narrow ionized discharge filaments initiates the conduction of electrons toward the more positive electrode, and ions towards the more negative electrode, although the mobility of the electrons is greater than that of the ions. An electrical charge accumulates on the dielectric layer(s) at the end(s) of each ionized filament; and, the voltage drop across the ionized filament reduces until the voltage falls below the discharge-sustaining level, so that the discharge is extinguished. The duration of the filamentary discharge is believed to be quite short: of the order of 100 nanoseconds or less. However, the resultant reactive species may have a significantly longer lifetime. The low charge mobility along the surface of the dielectric also limits the lateral region over which the gap voltage is diminished, so that a plurality of filaments may form in close proximity to one another.

Figure 1:
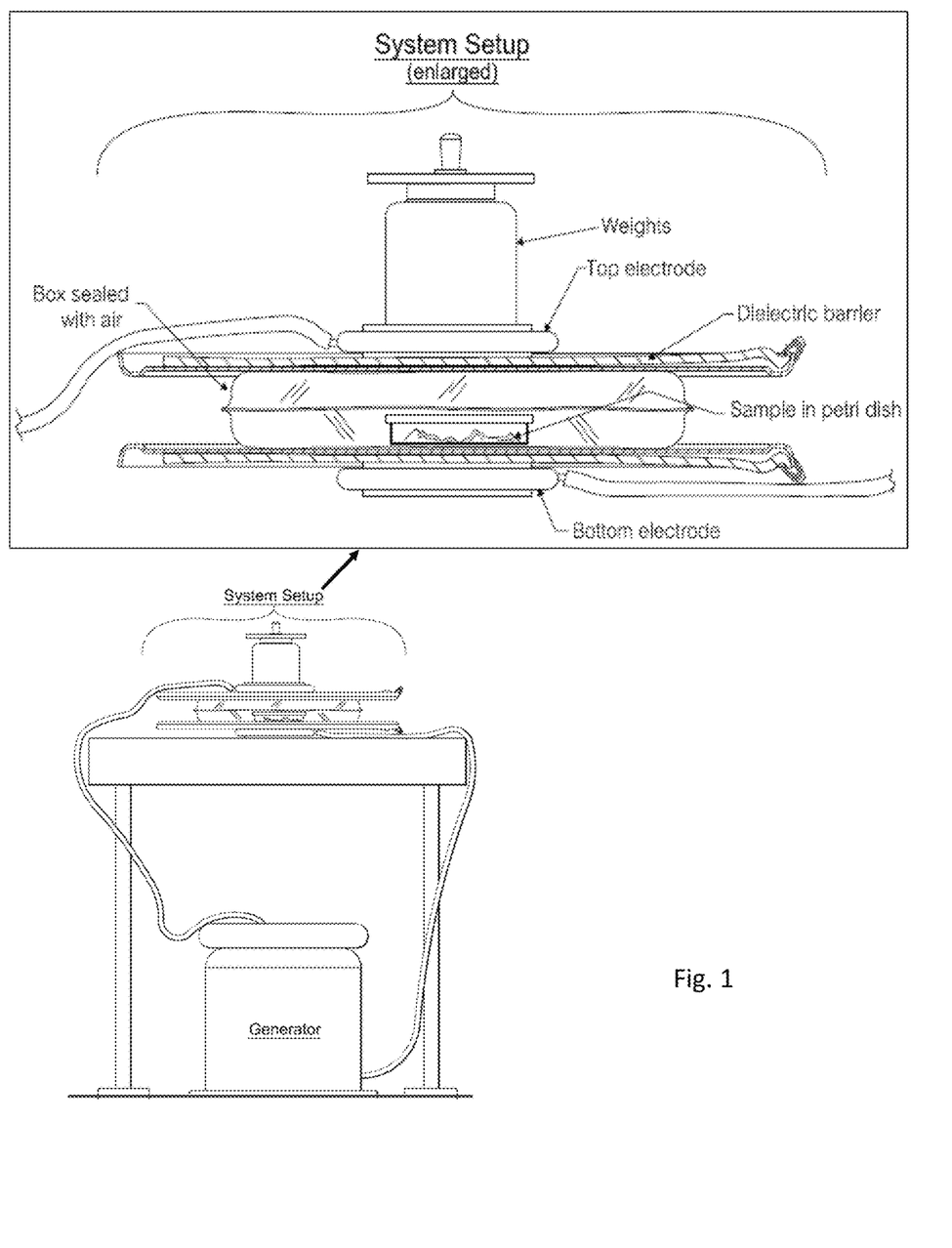
FIG. 1 is a system setup for treatment of coconut water using high voltage atmospheric cold plasma.

An experimental apparatus for treating a sample is shown in FIG. 1. A liquid object to be treated is placed substantially closed to and between the two dielectric barriers connected to a high voltage generating system in a defined compartment. The compartment is filled with air, a single or mixed gases, including, but not limited to $O_2$, $N_2$, $CO_2$, $H_2O$, $Cl_2$, as well as noble gases. The defined compartment should have an ability to substantially retain the reactive species that are the residual of the generated ANEP plasma for a period of time that is sufficient for a particular treatment process. The working gas, which may be air, or a modified mixture M65 (composition 65% $O_2$, 30% $CO_2$, 5% $N_2$), may be introduced into the compartment prior to treatment.

Working gas here means a gas either pure or in combination with other gases which can be used to generate plasma when an electrical field is applied to it. Different selection of working gases and working gas mixtures will affect the species present in the reactive gas produced by the HVCP. Further examples of gases which may be used to prepare the HVCP include oxygen ($O_2$); nitrogen ($N_2$); water vapor ($H_2O$); inert and noble gases such as helium (He), neon (Ne), argon (Ar), krypton (Kr), xenon (Xe) and sulfur hexafluoride ($SF_6$); hydrogen ($H_2$); carbon dioxide ($CO_2$) and carbon monoxide (CO); halogens and pseudohalogens such as fluorine ($F_2$), chlorine ($Cl_2$), bromine ($Br_2$), and cyanogen ($(CN)_2$); acidic gases such as hydrogen sulfide ($H_2S$), hydrogen fluoride (HF), hydrogen chloride (HCl), and carbonyl sulfide (COS); ammonia ($NH_3$); hydrazine ($N_2H_4$); nitrogen trifluoride ($NF_3$); chlorine dioxide ($ClO_2$); hydrocarbons such as methane ($CH_4$), ethane ($C_2H_6$) and acetylene ($C_2H_2$); alcohols such as methanol ($CH_3OH$) and ethanol ($C_2H_5OH$); and mixtures thereof. Preferred gases include air and MA65 (a mixture of 65% $O_2$, 30% $CO_2$, and 5% $N_2$). Increasing the amount of water vapor in the gas may be used to reduce ozone present in the reactive gas. Increasing the amount of noble gas, such as helium, may be used to reduce the voltage needed to produce the HVCP. The pressure of the gas use to prepare the HVCP is conveniently selected as ambient or atmospheric pressure, but other pressures may be used, such as 10 to 50000 Torr, more preferably 100 to 1000 Torr, such as 760 Torr (atmospheric pressure).

Experimental Procedure

First, three different 25 mL of coconut water samples were inoculated with three different bacterial strains *Salmonella enterica* thyphimurium LT2, *Escherechi coli* ATCC25922 and *Listeria monocytogenes* ATCC19115 individually. The test sample solution is placed in a petri dish in a plastic box which was filled with either air or a modified air mixture (M65, comprising 65% $O_2$, 30% $CO_2$, and 5% $N_2$). The system is sealed by a plastic bag and the bag was then positioned between two electrodes separated by dielectric barrier. The sample in petri dish was aligned under the electrodes for direct treatment. To understand the mechanism of how liquid foods interact with plasma and hinder microbial reduction a simulated mix of coconut water was developed and treated under the same experimental conditions.

Figure 2:
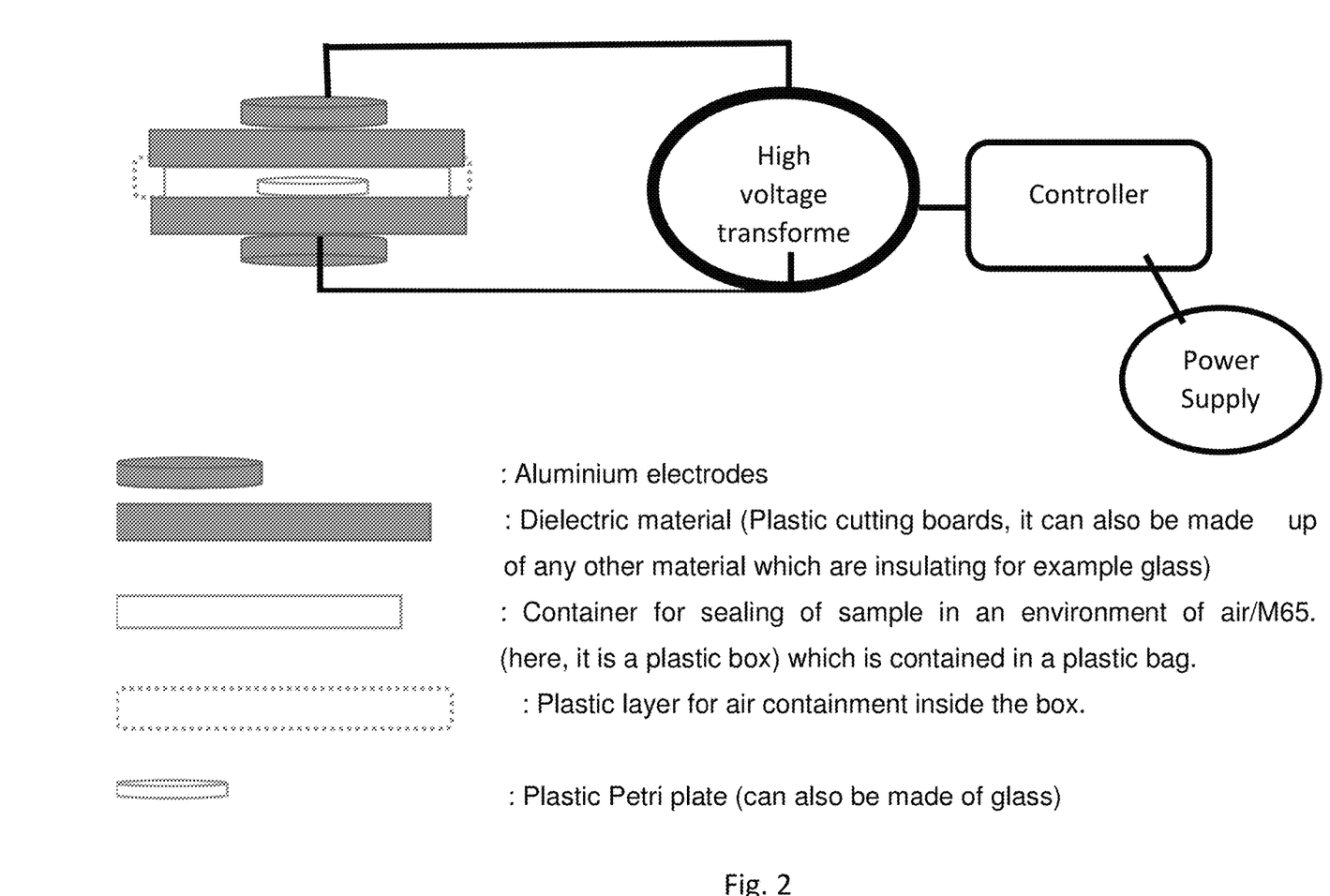
FIG. 2 is a schematic drawing of the system setup for inactivating pathogenic microorganisms in a liquid product using high voltage cold plasma.

Treatment time: 2 min at 90 kV than stored under refrigeration for 24 hours before analysis for microbial reduction (The system pictures and schematic diagram are shown in FIGS. 1 & 2). The colony counts were done by drop plate technique on selective enriched media for individual microorganisms both before and after treatment. Further the experiments with coconut water inoculated with bacteria were carried out with the addition of citric acid.

Method to Calculate Microbial Reductions: Innoculation:

To 100 ml of sample volume 1250 of bacterial cell media was added and mixed. The individual bacterial cultures were grown over night before the day of experiment.

Colony Counts:

To count the initial cell number the sample is serially diluted to ($10^0$, $10^1$, and $10^4$) used drop plate technique to plate 10 μL to grow the bacterial cells on the specific bacterial media plates. The plates were than kept for 24 hours at incubation at 37° C. after which the colonies were manually counted. Similar protocol was followed for both control and treated samples to obtain the colony counts. An example is shown in Table 1 below for experimental reduction of *E. coli* OH157:H7 with air plasma on coconut water inoculated with 400 ppm citric acid, 2 min at 90 kV.

TABLE 1

Reduction of *E. coli* OH157:H7 with air plasma on coconut water inoculated with 400 ppm citric acid, 2 min at 90 kV.

| Coconut water + 400 ppm citric acid | *E. coli* OH157:H7 strain reduction | | | | | Cfu/mL* | Average | log (Cfu/mL) | log reduction |
|---|---|---|---|---|---|---|---|---|---|
| Dilution | $10^0$ | $10^1$ | $10^2$ | $10^3$ | $10^4$ | | | | |
| Initial | UC | UC | UC | UC | 3 | 3000000 | 2500000 | 6.39** | |
| Initial | UC | UC | UC | UC | 2 | 2000000 | | | |
| Control | UC | UC | UC | UC | 5 | 5000000 | 3500000 | 6.54 | |
| Control | UC | UC | UC | UC | 2 | 2000000 | | | |
| Final | 2 | | | | | 200 | 200 | 2.30 | 4.09 |
| Final | 2 | | | | | 200 | | | |

*Cfu/ml = number of colonies on the plate × dilution × volume plated × 100, wherein: Dilution = $10^4$, Volume plated = 10 μl, and Log reduction = log(initial Cfu/ml) − log(final Cfu/mL) (The used values are shown in bold for better understanding);
**UC = Uncountable.

System Description

The system compromises two aluminum electrodes separated by dielectric barriers (i.e. insulating materials). The shape of electrodes, the working gas, the targeted plasma effect all are taken into account when selecting an operational voltage, voltage gradient, and dielectric material assembly. The electrodes are connected to a high voltage transformer and the voltage is controlled by a controller and the system is converted to electrical power supply. The sample to be treated is kept in a petri plate kept in a sealed container.

Experimental data demonstrated that air or M65 plasma treatment of coconut water did not result in the standard 5-log reduction. A simulated coconut water mix was developed in order to evaluate what components effect the efficacy of the plasma treatment. The simulated coconut water mix is composed of various mineral salts (potassium chloride, calcium chloride, magnesium chloride and monobasic sodium phosphate), organic acids (malic acid, citric acid and ascorbic acid), sugars (glucose, fructose), egg white protein, and fats. The mixture is adjusted to a pH 6.5 similar to the natural coconut water. The concentration of each individual component was designed following a literature reference (Young et al., *Molecules*, 14, 5144-5164, 2009). It was discovered that phosphates caused the major reduction in the efficiency of the cold plasma treatment. Furthermore, it was found that addition of citric acid to the mixture could lead to the standard 5-log reduction with a concentration from about 400 ppm to about 2000 ppm up on plasma treatment. Mere adding of citric acid at those concentration to the mixture did not lead to the killing of the microorganisms.

Yet in another experiment, it was further discovered that addition of about 200 ppm of ascorbic acid to the mixture markedly increase the bactericidal efficiency of the cold plasma treatment under identical conditions.

Figure 3:
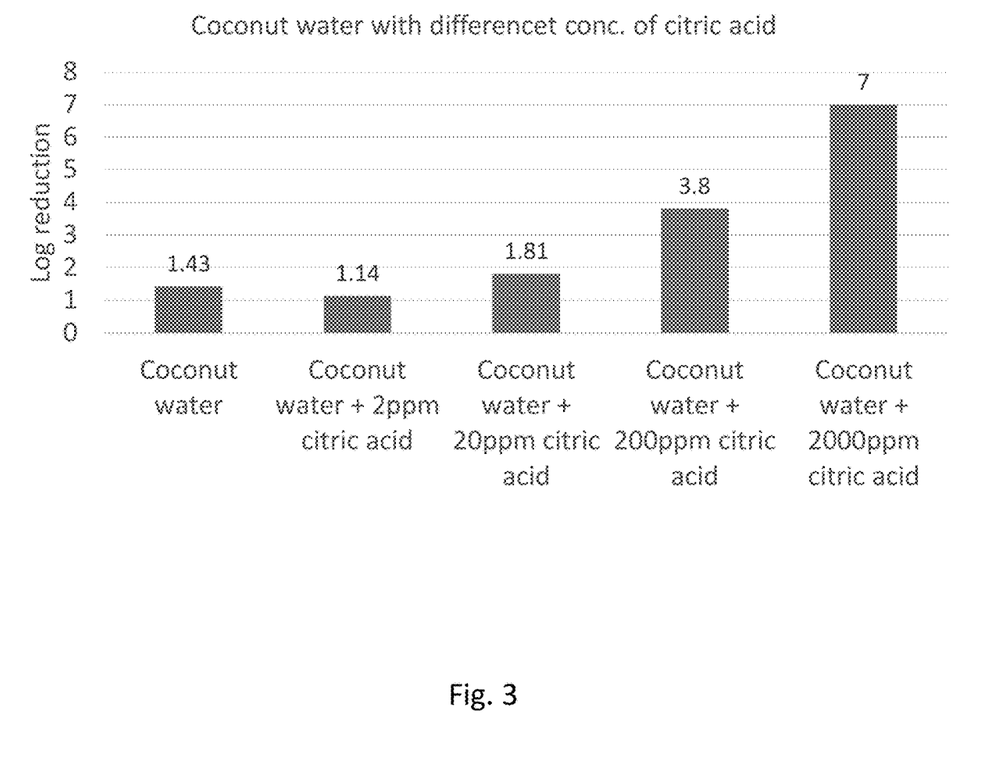
FIG. 3 shows the effects of citric acid concentrations on the reduction of *Salmonella* sp. upon cold plasma treatment (2 min at 90,000 volts air plasma).
Figure 4:
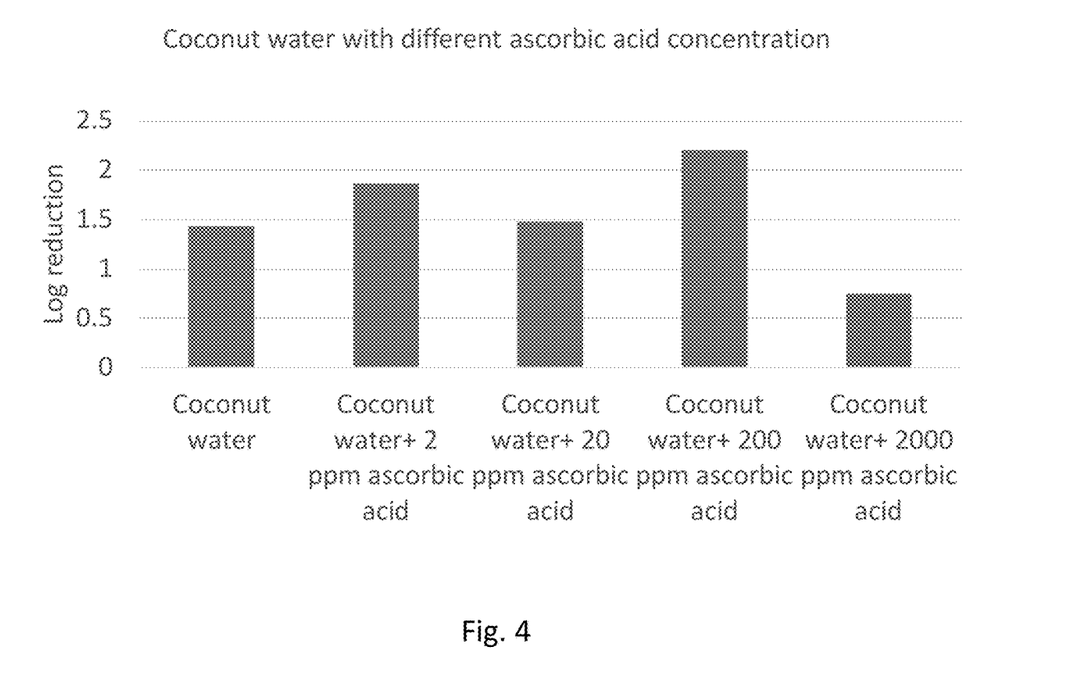
FIG. 4 shows the effects of ascorbic acid at 200 ppm on the reduction of *Salmonella* sp. upon cold plasma treatment (2 min at 90,000 volts air plasma).

The impacts of the concentrations of citric acid and ascorbic acid on the bactericidal efficiency of cold plasma treatment The concentrations of citric acid and ascorbic acid in coconut water from 2 ppm to 2000 ppm were studied and shown in FIGS. 3 and 4. It was discovered that 5-log reduction of *Salmonella* sp. could be achieved with one 30-sec cold plasma treatment by adding 2000 ppm of citric acid to the coconut water. On the other hand, the same bacteria reduction efficient was obtained with one 2-min treatment by adding 400 ppm of citric acid.

TABLE 2

Reduction in treatment plasma treatment time due to addition of 2000 ppm citric acid in coconut water (at 90 kv, air plasma)

| Sample | Time of treatment | Log reduction* |
| --- | --- | --- |
| Coconut water | 60 s | 0.88 ± 0.10 |
| Coconut water | 120 s | 1.3 ± 0.40 |
| Coconut water + 2000 ppm citric acid | 30 s | >5 |
| Coconut water + 2000 ppm citric acid | 60 s | >5 |
| Coconut water + 2000 ppm citric acid | 120 s | >5 |

*All experiments done in duplicates.

Table 3 shows the effect of various components on microbial reduction in various combinations with added magnesium chloride and sodium phosphate.

| No. | Solutions | pH | Initial microbial counts (log cfu/ml) | Final microbial counts (cfu/ml)* |
| --- | --- | --- | --- | --- |
|  | Distilled water | 6.9 | 9.23 ± 0.12 | 0 |
| 1 | 2.5 g Glucose + 2.5 g Fructose in 100 ml water | 6.6 | 7.18 ± 0.01 | 0 |
| 2 | 200 mg KCl + 27.35 mg $CaCl_2$ in 100 ml water | 7.1 | 6.79 ± 0.08 | 0 |
| 3 | 0.12 g egg albumin in 100 ml water | 6.2 | 6.93 ± 0.07 | 0 |
| 4 | 0.07 g soybean oil in 100 ml water | 6.5 | 6.74 ± 0.12 | 0 |
| 5 | 2.5 g glucose + 2.5 g fructose + 200 mg KCL + 27.35 mg $CaCl_2$ + 0.12egg albumin + 0.07 soybean oil in 100 ml water | 6.5 | 6.74 ± 0.08 | 0 |
| 6 | 2.5 g glucose + 2.5 g fructose + 200 mg KCL + 27.35 mg $CaCl_2$ + 0.12egg albumin + 0.07 soybean oil in 100 ml water(buffered with 1% $Na_2CO_3$) | 7.5 | 6.73 ± 0.24 | 0 |
| 7 | 2.5 g glucose + 2.5 g fructose + 200 mg KCL + 27.35 mg $CaCl_2$ + 0.12egg albumin + 0.07 soybean oil in 100 ml water(buffered with 1% $Na_2CO_3$) | 8.5 | 6.57 ± 0.04 | 0 |
| 8 | 2.5 g glucose + 2.5 g fructose + 200 mg KCL + 27.35 mg $CaCl_2$ + 37 mg $Na_2HPO_4$ + 30 mg $MgCl_2$ + 0.12egg albumin + 0.07 soybean oil in 100 ml water(buffered with 1% $Na_2CO_3$) | 7.5 | 7.47 ± 0.16 | 4.99 ± 0.18 (logcfu/ml) |

*All treatment were carried out using air as the working gas and treated for 2 min at 90 kV and stored for 24 hours under refrigeration. The data suggests that addition of magnesium and phosphates hinders microbial inactivation.

TABLE 4

Data showing microbial reduction in coconut water and simulated mix with and without citric acid when treated with both air and modified air (M65) plasma. (Treatment time 2 min at 90 kV)

| *Salmonella enterica* LT2 | Initial (log cfu/ml) | | Control (log cfu/ml) | | Log reduction* | |
| --- | --- | --- | --- | --- | --- | --- |
|  | Air | M65 | Air | M65 | Air | M65 |
| Coconut water | 7.04 ± 0.07 | 6.90 ± 0.05 | 7.21 ± 0.01 | 7.21 ± 0.01 | 1.30 ± 0.40 | 3.00 ± 0.12 |
| Coconut water + 400 ppm citric acid | 5.77 ± 0.21 | 5.77 ± 0.21 | 6.06 ± 0.02 | 6.02 ± 0.02 | >5 | >5 |
| Simulant Mix |  |  |  |  | 1.41 ± 0.26 | 3.7 ± 0.62 |
| Simulant Mix + 400 ppm citric acid |  |  |  |  | >5 | >5 |

TABLE 4-continued

Data showing microbial reduction in coconut water and simulated mix with and without citric acid when treated with both air and modified air (M65) plasma. (Treatment time 2 min at 90 kV)

| | Initial (log cfu/ml) | | Control (log cfu/ml) | | Log reduction | |
|---|---|---|---|---|---|---|
| | Air | M65 | Air | M65 | Air | M65 |
| *E. coli* OH157:H7 | | | | | | |
| Coconut water | 5.81 ± 0.04 | 5.81 ± 0.04 | 6.13 ± 0.02 | 6.10 ± 0.06 | 1.09 ± 0.17 | 1.79 ± 0.21 |
| Coconut water + 400 ppm citric acid | 6.39 ± 0.12 | 6.39 ± 0.12 | 6.54 ± 0.28 | 6.38 ± 0.12 | 4.09 ± 0.00 | >5 |
| Simulant Mix | | | | | 3.25 | >5 |
| Simulant Mix + 400 ppm citric acid | | | | | >5 | >5 |
| *E. coli* ATCC 25922 | | | | | | |
| Coconut water | 6.77 ± 0.10 | 6.77 ± 0.10 | 7.02 ± 0.14 | 6.96 ± 0.16 | 2.23 ± 0.33 | >5 |
| Coconut water + 400 ppm citric acid | 6.84 ± 0.00 | 6.84 ± 0.00 | 6.89 ± 0.03 | 6.92 ± 0.03 | >5 | >5 |
| Simulant Mix | | | | | 3.8 | >5 |
| Simulant Mix + 400 ppm citric acid | | | | | >5 | >5 |
| *Listeria monocytogenes* ATCC19115 | | | | | | |
| Coconut water | 6.47 ± 0.00 | 6.47 ± 0.00 | 6.6 ± 0.15 | 6.5 ± 0.28 | 2.03 ± 0.05 | >5 |
| Coconut water + 400 ppm citric acid | 6.47 ± 0.00 | 6.47 ± 0.00 | 6.54 ± 0.08 | 6.60 ± 0.00 | 2.39 ± 0.21 | >5 |
| Simulant Mix | | | | | >5 | >5 |
| Simulant Mix + 400 ppm citric acid | | | | | >5 | >5 |

*All the experiments were done in duplicates.

In summary, while phosphates in the simulated mix significantly reduced the bactericidal efficacy, addition of organic acids, such as citric acid or ascorbic acid, did lead to a much improved bactericidal efficiency of the cold plasma treatment process. The same effects was also observed in the cold plasma treatment of coconut water. That the combination of added organic acids with the high voltage atmospheric cold plasma process lead to a much improved bactericidal efficiency makes it possible and practical to meet the standards promulgated by FDA for food and feed industries.

The actual mechanism of the enhanced bactericidal efficiency due to the added citric acid has not been clearly elucidated. It is speculated that new chemical entities might have been by plasma treatment, which in turn help to increase the microbe-killing efficiency of this process. An optimized condition to achieve 5-log reduction of microbes in coconut water is to add 400 ppm of citric acid in combination with a high voltage cold plasma treatment for 2 min at 90 kV using modified air (M65) as the medium for plasma generation.

In the case for ascorbic acid, it was found that 200 ppm of the acid lead to a marked increase in antibacterial activity of the high voltage cold plasma treatment. Thus the combination of an organic acid with a high voltage atmospheric cold plasma treatment provide a new, practical, and efficient process to prepare safe liquid food products. This technology of high voltage cold plasma in combination with organic acid treatment may logically find applications in food, feed, medical, pharmaceutical, and healthcare industries. Some non-food liquid products may include cleaning, washing, or dressing solutions for medical, or pharmaceutical, or household uses.

Some liquid food products may include water, carbonated water, coconut water, tender coconut water, fruit juices, vegetable juices, mixed fruit juices, mixed vegetable juices, mixed fruit and vegetable juices, sports drinks, saline water, rehydration liquid formulations, milk, liquid milk products, alcoholic beverages, including beer, wines, ciders, or the like.

It is understood that multiple cycles of the cold plasma treatments may be required for certain types of products to meet enhanced requirements due to statutory or regulatory mandates, such as food products for the young, geriatric, or infirm population of people or animals.

It is understood that the process disclosed herein may be used independently or used in combination with other Hurdle technology, including thermal (low temperature long time, high temperature short time treatments, etc.) or non-thermal technologies (high pressure processing, microfiltration, carbonation, chlorination, ozonisation, ohmic heating, and the like) to treat liquid products.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A process for manipulating a liquid product using high voltage atmospheric cold plasma (HVACP), comprising the steps of:
   a. adding an acidic component to or adjusting an acidic component of a product to a final concentration from about 10 ppm to about 50,000 ppm;
   b. setting up a defined compartment filled with a working gas and an electric system for generating atmospheric cold plasma (ACP);
   c. generating ACP by applying a high electric voltage through a controller; and
   d. exposing said product to said ACP in said defined compartment.

2. The process of claim 1, wherein said ACP is generated by applying an electric voltage from about 30,000 volts to about 120,000 volts, between two dielectric barriers for a period of time.

3. The process of claim 1, wherein said manipulating is to inactivate or kill pathogenic and non-pathogenic microorganisms in said liquid product for consumption by human or animal.

4. The process of claim 1, wherein said working gas is a single or a mixture of combined gases comprising air, hydrogen, nitrogen, oxygen, carbon dioxide, and noble gases.

5. The process of claim 4, wherein said working gas is air.

6. The process of claim 4, wherein said working gas is a modified air comprising about 65% oxygen, about 30% carbon dioxide, and about 5% nitrogen.

7. The process of claim 1, wherein said acid component is selected from the group consisting of acetic acid, ascorbic acid, benzoic acid, carbonic acid, citric acid, glutamic acid, glycolic acid, hydrochloric acid, lactic acid, malic acid, oxalic acid, propionic acid, tartaric acid, natural amino acids, or a combination of two or more of said acids.

8. The process of claim 7, wherein said acid component is citric acid or ascorbic acid.

9. The process of claim 1, wherein said product is a food or drink product for consumption by human or animal.

10. The process of claim 1, wherein said liquid product is a liquid product for cleaning, washing, or dressing for food, feed, medical, pharmaceutical, or household uses, or a liquid product for consumption by human or animal.

11. The process of claim 1, wherein said liquid product is a liquid product selected from the group of water, carbonated water, coconut water, tender coconut water, fruit juices, vegetable juices, mixed fruit juices, mixed vegetable juices, mixed fruit and vegetable juices, sports drinks, saline water, rehydration liquid formulations, milk, liquid milk products, alcoholic beverages, and fermented beverages.

12. The process of claim 1, wherein said liquid product is water or coconut water.

13. A liquid product prepared using high voltage atmospheric cold plasma (HVACP), according the process of:
   a. adding an acidic component to or adjusting an acidic component of a product to a final concentration from about 10 ppm to about 50,000 ppm;
   b. setting up a defined compartment filled with a working gas and an electric system for generating atmospheric cold plasma (ACP);
   c. generating ACP by applying a high electric voltage through a controller; and
   d. exposing said product to said ACP in said defined compartment.

14. The product of claim 13, wherein said liquid product is a liquid product for cleaning, washing, or dressing for food, feed, medical, pharmaceutical, or household uses, or a liquid product for consumption by human or animal.

15. The product of claim 14, wherein said liquid product is a liquid food product comprising water, carbonated water, coconut water, tender coconut water, fruit juices, vegetable juices, mixed fruit juices, mixed vegetable juices, mixed fruit and vegetable juices, sports drinks, saline water, rehydration liquid formulations, milk, liquid milk products, alcoholic beverages, including beer, wines, ciders, or the like.

16. The product of claim 15, wherein said liquid product is water or coconut water.

17. The product of claim 13, wherein said acidic component comprises acetic acid, ascorbic acid, benzoic acid, carbonic acid, citric acid, glutamic acid, glycolic acid, hydrochloric acid, lactic acid, malic acid, oxalic acid, propionic acid, tartaric acid, natural amino acids, or a combination of two or more of said acids.

18. The product of claim 13, wherein said working gas is a single or combined gases including, but not limited to, air, hydrogen, nitrogen, oxygen, carbon dioxide, noble gases, or a combination thereof.

19. The product of claim 13, wherein said working gas is air.

20. The product of claim 13, wherein said working gas is a modified air comprising about 65% oxygen, about 30% carbon dioxide, and about 5% nitrogen.

21. The product of claim 13, wherein said ACP is generated by applying an electric voltage from about 30,000 volts to about 120,000 volts, between two dielectric barriers for a period of time.

* * * * *